(12) United States Patent
Osborne et al.

(10) Patent No.: US 7,749,196 B2
(45) Date of Patent: Jul. 6, 2010

(54) SMALL GAUGE NEEDLE CATHETERIZATION APPARATUS

(75) Inventors: Thomas A. Osborne, Bloomington, IN (US); David G. Burton, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 1772 days.

(21) Appl. No.: 10/879,409

(22) Filed: Jun. 29, 2004

(65) Prior Publication Data
US 2005/0004523 A1    Jan. 6, 2005

Related U.S. Application Data

(60) Provisional application No. 60/484,414, filed on Jul. 2, 2003.

(51) Int. Cl.
*A61M 5/178*    (2006.01)
(52) U.S. Cl. .................................. 604/164.01
(58) Field of Classification Search ............. 604/93.01, 604/158, 164.01, 192, 264, 272, 164.1, 164.12, 604/164.11, 164.13, 523, 528
See application file for complete search history.

(56) References Cited

U.S. PATENT DOCUMENTS

| | | | | |
|---|---|---|---|---|
| 4,650,472 A | | 3/1987 | Bates | |
| 5,295,974 A | * | 3/1994 | O'Laughlin | 604/198 |
| 5,489,269 A | | 2/1996 | Aldrich et al. | |
| 5,573,520 A | | 11/1996 | Schwartz et al. | |
| 5,702,373 A | | 12/1997 | Samson | |
| 5,891,112 A | * | 4/1999 | Samson | 604/524 |
| 5,911,715 A | * | 6/1999 | Berg et al. | 604/525 |
| 6,048,339 A | * | 4/2000 | Zirps et al. | 604/525 |

FOREIGN PATENT DOCUMENTS

| | | | |
|---|---|---|---|
| EP | 0 808 637 A3 | | 3/1998 |
| WO | WO2005/046778 | * | 5/2005 |

\* cited by examiner

*Primary Examiner*—Nicholas D Lucchesi
*Assistant Examiner*—Christopher D Koharski
(74) *Attorney, Agent, or Firm*—Brinks Hofer Gilson & Lione

(57) ABSTRACT

An apparatus for percutaneous catheterization. The apparatus comprises a catheter, and an inner cannula received within the lumen of the catheter. The inner cannula has a distal portion that tapers toward the distal end, and is sized to extend through the distal opening of the catheter to provide a generally smooth diametrical transition between the distal end of the catheter and the distal open end of the inner cannula. A stiffening cannula is sized to be received in the lumen of the inner catheter, and has an inner diameter sized to receive a wire guide therethrough. The stiffening cannula as a distal section of greater flexibility than the flexibility of a proximal section for providing kink resistance to the apparatus.

20 Claims, 3 Drawing Sheets

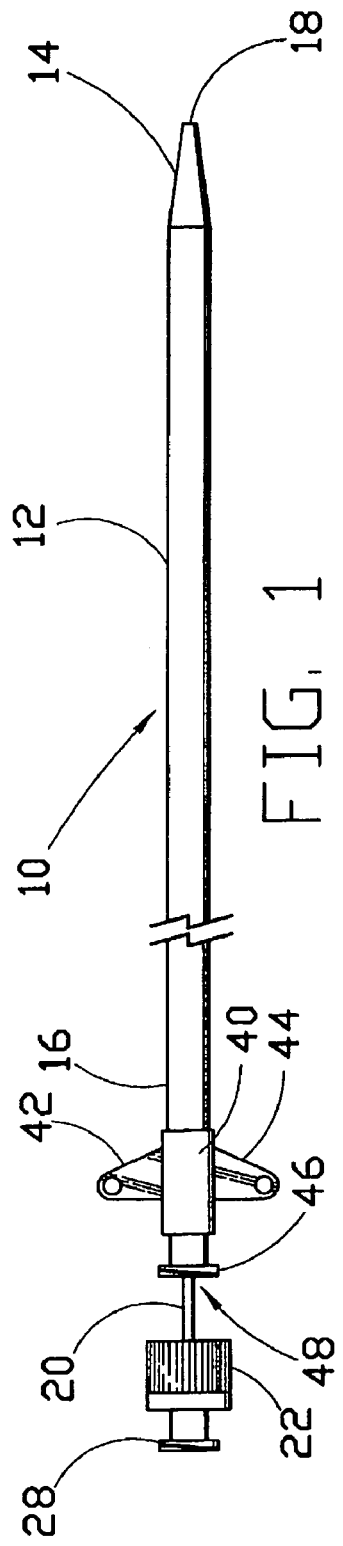
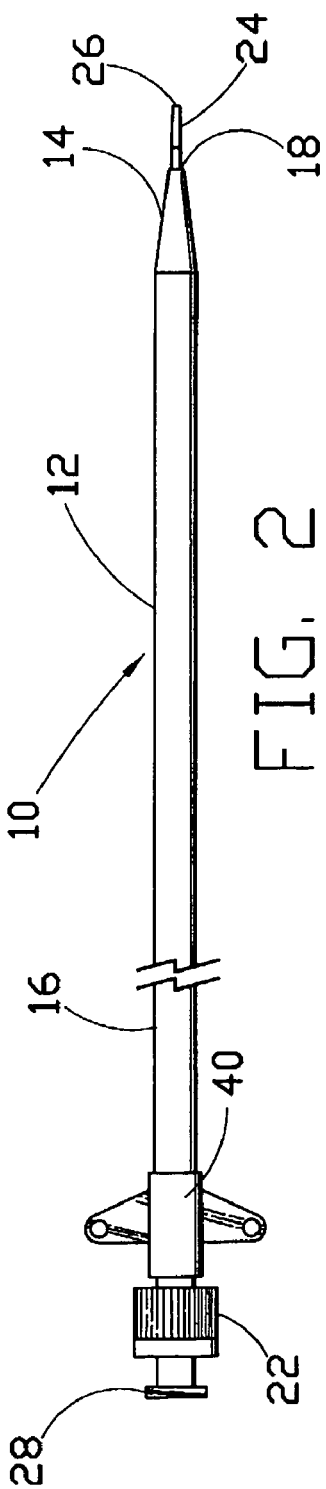
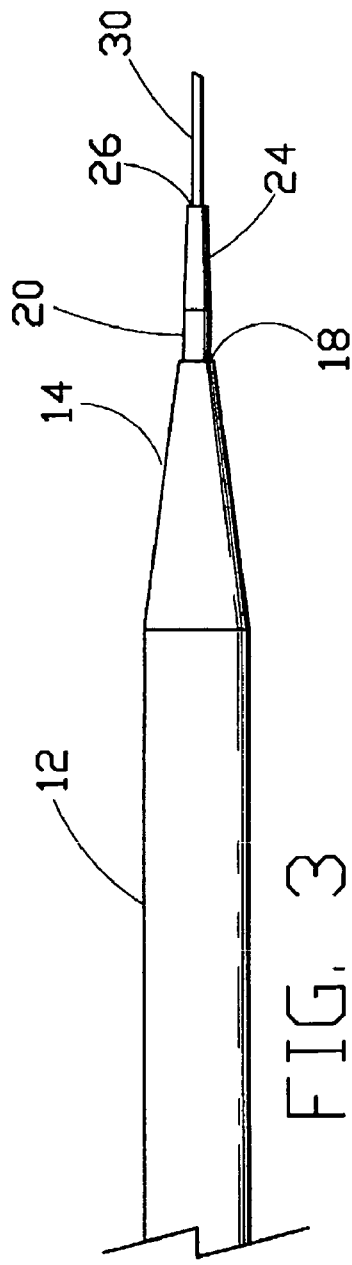

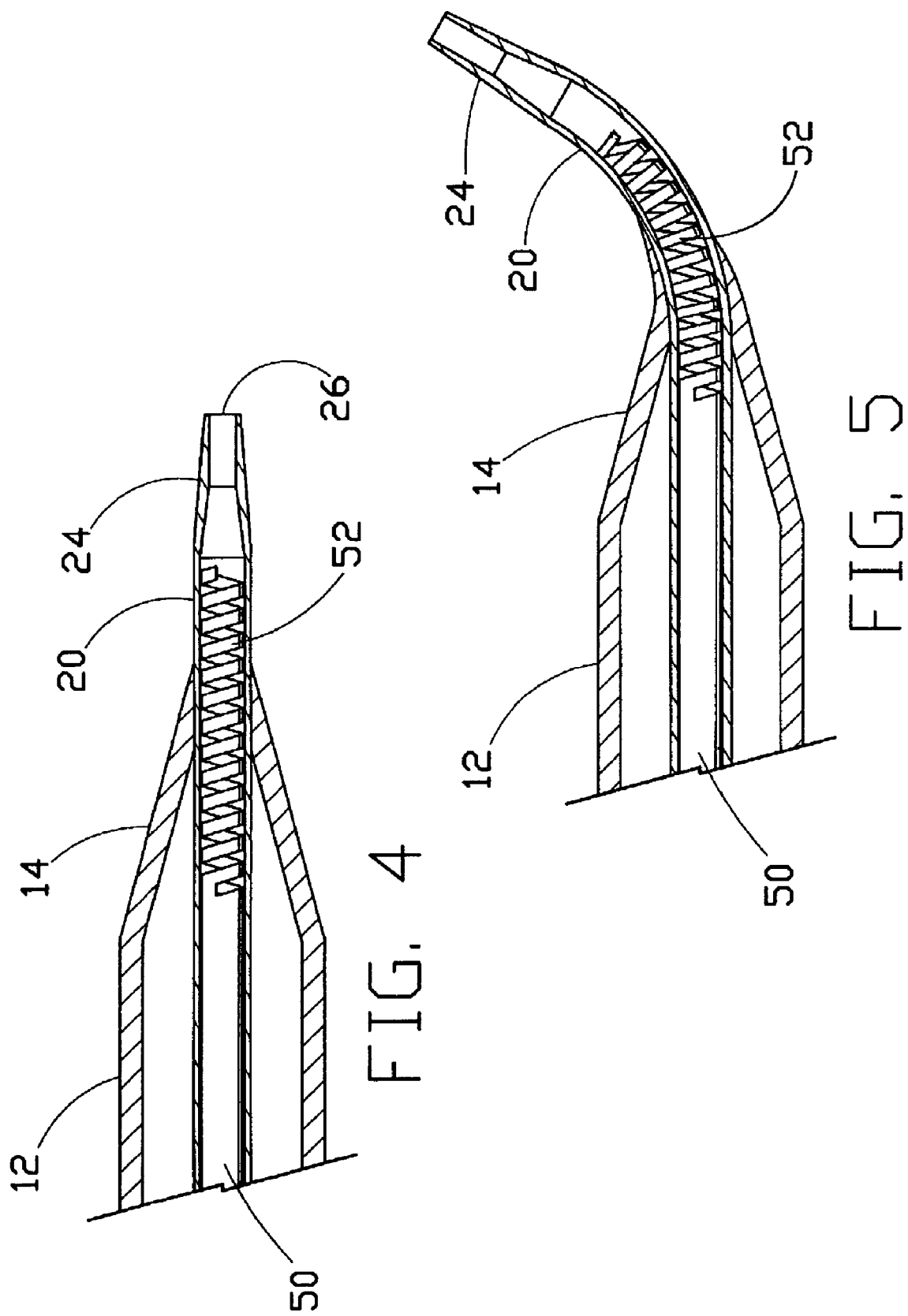

SMALL GAUGE NEEDLE CATHETERIZATION APPARATUS

RELATED APPLICATION

The present patent document claims the benefit of the filing date under 35 U.S.C. §119(e) of Provisional U.S. Patent Application Ser. No. 60/484,414, filed Jul. 2, 2003, which is hereby incorporated by reference.

BACKGROUND

1. Technical Field

The present application relates to the field of percutaneous catheterization of blood vessels.

2. Background Information

Many medical procedures require the percutaneous placement of a medical device, such as a catheter, in a vein or an artery. Such catheters are used for, among other things, blood pressure monitoring, blood sampling and the administration of drugs and fluids to a patient.

Typically, such catheters are introduced using the well-known Seldinger percutaneous entry technique. In the Seldinger technique, the physician makes an oblique entry into the vein or artery with a beveled needle. A wire guide is then inserted through the bore of the needle about 5 to 10 cm into the passageway. The needle is thereafter withdrawn, leaving the wire guide in place. The catheter is inserted over the wire guide, and advanced through the skin into the vein or artery at the needle puncture site. Once the catheter is in place, the wire guide is withdrawn.

Conventional wire guides are normally comprised of a tightly wound helical stainless steel wire coil. In order to have sufficient rigidity to properly support and lead many standard catheters and other interventional devices, such wire guides are typically constructed to have an outer diameter (O.D.) of about 0.035 or 0.038 inch (0.89 or 0.97 mm). The most common sized needle used for initial vascular access and introduction of a standard 0.035 or 0.038 inch wire guide is an 18 gauge (0.052 inch; 1.32 mm O.D.) thin-walled needle. The 18 gauge needle has become the standard needle for use with the Seldinger technique for percutaneous catheterization. However, the outer diameter of an 18 gauge needle is just large enough to cause bleeding or other organ damage if it does not enter the vessel correctly, or if it inadvertently penetrates some other organ.

Because of the unavoidable tissue trauma that results from insertion of a needle, particularly a lancet beveled needle of the type commonly used in the Seldinger technique, it would be desirable if a smaller needle could be used to effect the initial entry. A 22 or 21 gauge (0.028 inch or 0.032 inch; 0.72 mm or 0.81 mm O.D.) needle has an outer diameter that is small enough that regardless of where the needle goes, only minimal, if any, complications are likely to occur. In addition, needles having smaller outer diameters (such as 22 or 21 gauge needles), are generally provided with a correspondingly shorter bevel at the needle tip compared to the size of the bevel tip of an 18 gauge needle. It is easier to get a short bevel into the lumen of a small vessel than the longer bevel of the 18 gauge needle. Unfortunately, however, 22 and 21 gauge needles are not large enough to pass a standard 0.035 inch or 0.038 inch (0.89 mm or 0.97 mm) diameter wire guide therethrough. The largest wire guide that can be easily introduced into such small gauge needles is a wire of 0.018 inch (0.46 mm) outer diameter. However, as stated, many diagnostic and interventional devices need at least a 0.035 inch (0.89 mm), and more preferably a 0.038 inch (0.97 mm), diameter wire guide to be able to optimally introduce and manipulate such devices through the vasculature.

U.S. Pat. No. 4,650,472 ("the '472 patent"), assigned to the assignee herein, describes a catheterization apparatus which allows a smaller gauge needle, such as a 22 gauge (0.028 inch; 0.72 mm O.D.) needle, to be used for percutaneous insertion of standard catheters and catheter-introducing sheaths of up to a size of at least 9 French (0.118 inch; 3.0 mm). The '472 patent is incorporated by reference herein. In the apparatus described in the '472 patent, a removable inner cannula is provided over the wire guide but inside the catheter. This removable inner cannula has a tapered tip which extends through the distal opening of the catheter, and provides a diametrical transition between the large distal opening of the catheter and an 0.018 inch wire guide. The inner cannula is about 0.038 inch (0.97 mm) O.D., and the catheter is tapered to fit over the inner cannula. The catheter and the inner cannula are inserted into the blood vessel in unison, whereby the smooth diametrical transition of the leading end minimizes the trauma that may otherwise be caused by the insertion of the large diameter catheter over the small diameter wire guide in the absence of such a transition area. Once the catheter is properly positioned within the blood vessel, the inner cannula and the smaller wire guide can be withdrawn, leaving the catheter in place. A 0.035 or a 0.038 inch (0.89 or 0.97 mm) wire guide can then be introduced through the catheter and into the vessel.

Thus, the apparatus of the '472 patent can be successfully used to percutaneously insert a catheter into a blood vessel using a wire guide and an introducer needle which are much smaller in diameter than the distal opening of the catheter. This ensures good flow characteristics for the catheter and a minimum of tissue trauma to the patient. It also allows for the introduction of larger diagnostic and interventional devices than would otherwise be possible when an initial entry is made with a small diameter needle.

In many cases when a catheter is to be inserted, it is necessary to make the puncture through tough, fibrous tissue, such as scar tissue, muscle tissue and the like. In such cases it is sometimes desired to further enhance the rigidity or column strength of a two-part dilator system such as that described in the '472 patent, so that the apparatus can be more easily pushed through the puncture site and the vessel wall. In order to enhance this rigidity, it is known to position a thin needle stiffening cannula within the lumen of the inner cannula of the apparatus of the '472 patent. The stiffening cannula generally extends from the proximal end of the apparatus up to about 1 or 2 mm proximal of the distal end opening. This cannula provides extra stiffness to the apparatus without adding significant bulk, complexity or additional parts.

The apparatus described in the '472 patent, as well as the modified apparatus that includes the stiffening cannula, are available from Cook Incorporated, of Bloomington, Ind., and sold under the trademark MICROPUNCTURE®.

The addition of the stiffening catheter adequately stiffens the two-part apparatus described in the '472 patent device so that it can continue to be advanced in the vessel without buckling when it meets resistance. The presence of the stiffening cannula, however, may create an abrupt change in stiffness at the distal end of the apparatus, between the relatively hard stiffening cannula and the much softer inner cannula. This abrupt change in stiffness may cause a kink to form when the distal tip of the apparatus is subjected to a bending force, such as when the catheter is attempting to negotiate a tight bend within the vasculature. This prior art apparatus is shown in FIG. 6 of the present application. In the figure, a kink is shown at the distal portion 124 of inner cannula 120, immediately distal to the distal end of stiffening cannula 150. When an apparatus kinks in this manner, more resistance to insertion is created. As a result, the apparatus may become lodged and unable to be advanced further into the vessel. In severe cases, this abrupt transition may even result in the tip breaking off in the vessel.

It is desired to provide an apparatus for percutaneous catheterization in a blood vessel that avoids the problems of the prior art. In particular, it is desired to provide an apparatus for percutaneous catheterization that has a flexible distal end that avoids the abrupt change in stiffness in prior art devices. It is further desired to provide an apparatus for catheterization that is capable of allowing the initial introduction to be made by a small diameter needle and a small diameter wire guide, and yet enables a larger diameter wire guide to be inserted following withdrawal of the small diameter needle and a smaller wire guide. It is further desired to provide such an apparatus that has sufficient rigidity or column strength to enable the apparatus to readily pass through tough fibrous tissue, and that has a flexible distal tip portion that avoids the abrupt transition of prior art devices.

BRIEF SUMMARY

The present invention provides an apparatus for percutaneous catheterization in a blood vessel that addresses the problems of the prior art devices described above.

In one form of the present invention, the distal end of a stiffening cannula is modified so that it has a gradual decrease in stiffness. The tip of the apparatus is made sufficiently flexible to form a curve without kinking or breaking at the transition point from the polymer tip to the distal end of the inner cannula. In another form of the present invention, an inner sleeve is added to the inside of a stiffening cannula. The sleeve may extend past the distal end of the stiffening cannula to the distal end of the inner cannula. This sleeve protects the edge of the distal end of the stiffening cannula, and adds support or kink resistance to the transition from the stiffening cannula to the tip of the inner cannula.

Therefore, in one embodiment, there is provided an apparatus for percutaneous catheterization over a wire guide. The apparatus comprises a catheter having proximal and distal open ends, and having a lumen extending longitudinally therethrough. An inner cannula having proximal and distal open ends, and having a lumen extending longitudinally therethrough, is sized to be received within the lumen of the catheter. The distal open end of the inner cannula is sized to receive the wire guide therethrough. The inner cannula has a generally linear main body portion and a tapered distal portion, wherein the tapered distal portion has an outer diameter that decreases toward the cannula distal end and is sized to extend through the distal open end of the catheter to provide a generally smooth diametrical transition between the catheter and the wire guide. The apparatus further comprises a stiffening cannula having proximal and distal open ends, and having a lumen extending longitudinally therethrough. The lumen of the stiffening cannula is sized to receive the wire guide therethrough. The stiffening cannula is sized to be received within the lumen of the inner cannula, and extend along the generally linear body portion of the inner cannula to a terminal point. The stiffening catheter has a distal section of greater flexibility than the flexibility of a proximal section of the stiffening catheter.

In another embodiment, the present invention comprises an apparatus for percutaneous catheterization. The apparatus comprises a catheter having proximal and distal open ends, and having a lumen extending longitudinally therethrough. An inner cannula is provided having proximal and distal open ends, and having a lumen extending longitudinally therethrough. The inner cannula is sized to be received within the lumen of the catheter, and the distal open end of the inner cannula is sized to receive a wire guide therethrough. The inner cannula has a generally linear main body portion and a tapered distal portion. The tapered distal portion has an outer diameter that decreases toward the cannula distal end and is sized to extend through the distal open end of the catheter to provide a generally smooth diametrical transition between the catheter and the wire guide. A stiffening cannula having proximal and distal open ends, and having a lumen extending longitudinally therethrough is provided. The stiffening cannula is sized to be received within the lumen of said inner catheter. An inner sleeve having proximal and distal open ends, and having a lumen extending longitudinally therethrough is provided. The lumen of the inner sleeve is sized to receive the wire guide therethrough. The inner sleeve is sized to be received within the lumen of the stiffening cannula, wherein the inner sleeve distal end extends substantially to the distal opening of the inner cannula.

In yet another embodiment, the present invention comprises a method of percutaneous catheterization. In the inventive method, a wire guide is introduced into a vessel. A catheterization apparatus is provided. The catheterization apparatus comprises a catheter having a lumen extending longitudinally therethrough and having a distal end; an inner cannula having a lumen extending longitudinally therethrough, the inner cannula sized to be received within the lumen of the catheter, a distal end of the inner cannula tapering to a diameter just large enough to enable the wire guide to pass freely therethrough, the tapered distal end providing a generally smooth diametrical transition between the catheter and the wire guide; and a stiffening cannula having a lumen extending longitudinally therethrough, the lumen of said stiffening cannula sized to receive said wire guide therethrough, the stiffening cannula being sized to be received within the lumen of said the catheter, the stiffening catheter having a distal section of greater flexibility than the flexibility of a proximal section. The catheterization apparatus is introduced into the vessel over the wire guide. The wire guide, inner cannula and stiffening cannula are then withdrawn from the vessel, while maintaining the catheter in the vessel. If desired, a second wire guide having a larger outer diameter than the diameter of the first wire guide can then be inserted into the vessel through the lumen of the catheter following withdrawal of the first wire guide, inner cannula and stiffening catheter. A medical device that requires a larger wire guide can then be inserted into the vessel over the second wire guide. As a result, a medical device that requires a large wire guide for introduction into a vessel has been introduced even though an initial insertion is made with a small gauge needle and small wire guide.

BRIEF DESCRIPTION OF THE DRAWINGS

FIG. 1 is an elevational view of an apparatus for percutaneous catheterization according to an embodute of the present invention, showing a catheter and an inner cannula partially inserted into the catheter;

FIG. 2 is an elevational view of the apparatus of FIG. 1, showing the inner cannula fully inserted into the catheter;

FIG. 3 is an enlarged elevational view of the distal portion of the apparatus as shown in FIG. 2, and showing a wire guide extending from the distal end of the cannula;

FIG. 4 is a view of an embodiment of the present invention, wherein the catheter and inner cannula are shown in longitudinal cross section, and the stiffening cannula is not in cross section;

FIG. 5 illustrates the embodiment of FIG. 4 showing the smooth transition between the soft polymer tip and the stiff cannula when the distal tip of the apparatus is subjected to a bending force;

DETAILED DESCRIPTION OF THE DRAWINGS AND THE PRESENTLY PREFERRED EMBODIMENTS

Figure 6:
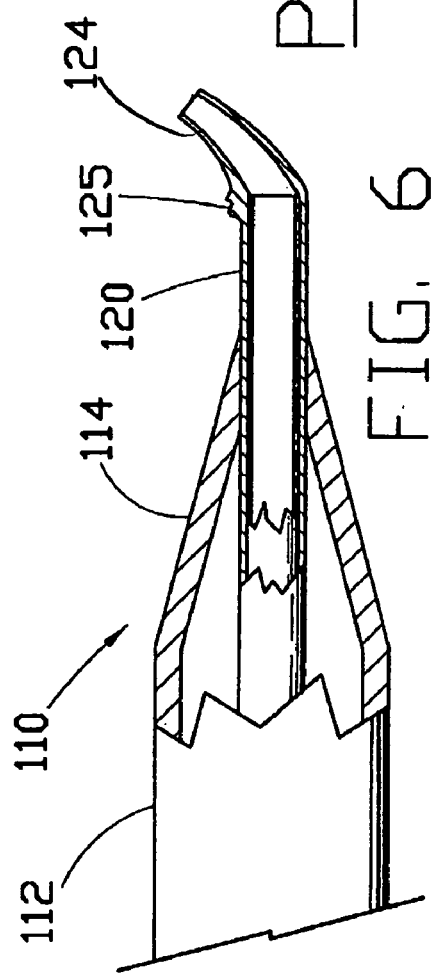
FIG. 6 is a longitudinal cross-sectional view of a prior art apparatus for effecting percutaneous catheterization.

For purposes of promoting an understanding of the present invention, reference will now be made to the embodiments illustrated in the drawings, and specific language will be used to describe the same. It is nevertheless to be understood that no limitation of the scope of the invention is thereby intended, the proper scope of the invention being indicated by the claims appended below and the equivalents thereof. The figures are not all drawn to the same scale to avoid obscuring the details of the finer structures. The following detailed description of the preferred embodiments will make clear the preferred arrangement, size relationships and manner of using the components shown herein.

Illustrated in FIG. 1 is an elevational view of an apparatus 10 for percutaneous catheterization. As shown in the view of FIG. 1, apparatus 10 includes a catheter 12 and an inner cannula 20. For convenience, the term "catheter" is used herein to refer to both catheters and catheter-introducing sheaths, as they are analogous structures for the purposes of this invention.

In the view of FIG. 1, inner cannula 20 is shown partially inserted into catheter 12. During a particular point in the preferred method of use of the inventive apparatus, cannula 20 is more fully disposed within catheter 12, as illustrated in FIG. 2 and as further discussed below. Preferably, catheter 12 comprises a polymeric elongated tubular structure in the range, e.g., of about French size 3 to 9, and having a lumen extending longitudinally therethrough. Catheter 12 is preferably formed of radiopaque polyethylene, although it can alternately be formed of materials such as polytetrafluoroethylene, vinyl, nylon, polyurethane and other conventional polymers and materials that are typically used for such purposes in the medical field. Catheter 12 is configured with a slight taper at distal end 14 terminating at distal opening 18. Distal opening 18 is significantly larger in diameter than wire guide 30 (FIG. 3), with a diameter of about 0.039 inch (1 mm) being typical. Wire guide 30 will typically have a diameter of about 0.018 inch (0.46 mm).

Apparatus 10 further includes a hub 40 having a pair of radially protruding wings 42, 44 fixed to proximal end 16 of catheter 12, as well as a standard Luer lock type connector 46. Wings 42, 44 can be used as anchor points for securing the catheter in place after it has been inserted, such as by taping them to the patient's skin. Hub 40 has a passageway therethrough in alignment with and communicating with the lumen of catheter 12, the passageway being at least as great in diameter as the lumen. The passageway through hub 40 terminates in proximal opening 48.

Also shown in FIG. 1 is inner cannula 20. Inner cannula 20 is sized to fit freely within the lumen of catheter 12. Cannula 20 is generally a soft polymeric tube having a lumen therethrough, the lumen of inner cannula 20 being sized to receive wire guide 30 freely therein. Attached to the proximal end of inner cannula 20 is connector hub 28 which terminates in a Luer lock connector 22. Luer connector 22 is configured to releasably engage and connect with Luer lock connector 46 to selectively maintain catheter 12 and cannula 20 in the fixed longitudinal relationship with respect to each other shown in FIG. 2. Connector hub 28 and Luer lock connector 22 have a passageway therethrough aligned with and communicating with the lumen of inner cannula 20. Hubs and connectors of the type described hereinabove with regard to catheter 12 and cannula 20 are well known in the medical arts, and need not be further described herein.

Referring again to FIG. 2, inner cannula 20 is shown disposed fully within catheter 12, and connector 22 is engaged with connector 46. In this arrangement, the distal tip 24 of inner cannula 20 extends through distal opening 18 of catheter 12. Inner cannula 20 terminates in distal opening 26, which is just slightly larger in diameter than wire guide 30, that is, it is just large enough to receive wire guide 30 freely therethrough.

FIG. 3 is an enlarged view of the distal end of catheter 12 showing the relationship of the distal portions of catheter 12 and cannula 20 to wire guide 30, when the catheter and cannula are engaged as in FIG. 2. Wire guide 30 is shown disposed within cannula 20 and extending through cannula distal opening 26. As can be seen, cannula tapered distal tip 24 provides a diametrical transition from distal opening 18 of catheter 12 to distal opening 26 of cannula 20. This provides a relatively smooth diametrical transition from wire guide 30 to the maximum diameter of catheter 12, when wire guide 30, cannula 20, and catheter 12 are arranged as shown. A relatively smooth transition such as that shown in the figure enables the apparatus to be percutaneously inserted into the vessel over the guide wire, in a manner that avoids the presence of larger diameter free edges that would otherwise be present at the site of the insertion.

FIG. 4 shows the distal portion of the apparatus of FIG. 2 wherein catheter 12 and inner cannula 20 are shown in longitudinal cross section, and stiffening cannula 50 is not in cross section. Stiffening cannula 50 is disposed within the lumen of inner cannula 20, and extends to a terminal point that does not extend beyond the distal end of the inner cannula. Preferably, the terminal point is between about 0.5 and 10 mm short of (e.g., proximal to) the distal end of the inner cannula, and more preferably, between about 1 and 2 mm short of said distal end. The inner diameter of stiffening cannula 50 is just slightly larger in diameter than wire guide 30, to provide a secure fit for stiffening cannula 50 within the lumen of inner cannula 20.

Stiffening cannula 50 is a needle-like elongated tube having sufficient rigidity to assist apparatus 10 in passing through tough, fibrous tissue. Preferably, stiffening cannula 50 is made from a relatively stiff polymer, such as PET. Alternatively, stiffening cannula 50 can be formed from a metal such as stainless steel, from a metallic alloy such as nitinol, or from a fiber composite material. Stiffening cannula 50 should be formed of a material that provides stiffness and yet also has a thin wall, so as to not add appreciably to the overall diameter. In the embodiment of FIG. 4, stiffening cannula 50 is provided with spiral shaped grooves 52. Grooves 52 may be cut into or otherwise formed at the distal end of stiffening cannula 50 to increase the flexibility of the distal end of the stiffening cannula.

FIG. 5 shows a view of the embodiment of FIG. 4 when a bending force is applied at the distal end of apparatus 10. Such forces are typically encountered when the apparatus negotiates a bend in the vasculature. As shown in the figure, when the tip is exposed to a bending force, a smooth bending transition results between the distal end 14 of catheter 12, the soft polymer tip 24 of inner cannula 20, and the stiffening cannula 50. The spiral-shaped grooves 52 of stiffening cannula 50 in effect convert the distal portion of cannula 50 into a helical spring. As a result, the distal tip portion of the apparatus becomes substantially kink resistant, and bends as shown in FIG. 5.

For purposes of comparison, FIG. 6 is a longitudinal cross-sectional view of a prior art apparatus 110. Prior art apparatus 110 is similar in certain respects to the inventive apparatus, as it includes a catheter 112, an inner cannula 120 and a stiffening cannula 150. Catheter 112 includes distal end 114, and inner cannula 120 includes distal end 124. Stiffening cannula 150, however, does not include any grooves or other structure that imparts increased distal flexibility. The prior art apparatus 110 is shown in FIG. 6 exposed to a distal bending force. Since this prior art apparatus does not include a distal portion of increasing flexibility as is present in the embodiment of FIG. 5, the application of the bending force creates an abrupt stiffness change at the distal tip from the stiff distal end of the stiffening cannula 150 to the soft distal tip 124 of the inner cannula 120. Such an abrupt change in stiffness may result in the formation of a bump or other restriction 125 at the joint between the rigid cannula body and the soft tip 124 of the inner cannula. Further, the soft cannula tip is prone to kinking and/or breaking off.

The spiral cut shown in FIGS. 4 and 5 includes similarly sized and spaced coil turns. Alternatively, however, the stiffening cannula can be formed to have coil turns spaced an increasing distance from each other, that is, at a greater pitch, as the cannula approaches the distal tip, to further increase the flexibility at the distal tip. As another alternative, the width and/or thickness of the material forming the separate coil turns can be decreased in sequential fashion toward the distal end of the apparatus, in order to still further decrease the flexibility toward the distal end of the device. The spiral shaped grooves can be formed in the distal portion of stiffening cannula 50 by any means well known in the art, such as by laser cutting the grooves into the cannula.

Although the embodiment of FIGS. 4 and 5 utilizes spiral cut slots to provide the portion of increased flexibility, other known mechanisms for providing a transition from a stiff portion to a more flexible portion may be substituted for the spiral cut slots. For example, a taper can be ground on the distal end of the stiffening cannula. The taper reduces the thickness of the cannula wall, thereby imparting additional flexibility at the reduced thickness portion. Alternatively, one or more short distal segments of increasing flexibility (in the distal direction) can be adhered to the distal end of a stiffening cannula by conventional means, such as heat or glue bonding, to increase distal flexibility. The distal tip of the stiffener can also be made flexible by adhering a wire coil to the inner surface of a stiffening cannula.

Alternatively, increased distal flexibility could also be attained by cutting a series of parallel slots, either transversely or longitudinally, along the distal portion of the stiffening cannula. The slots could go, for example, from about halfway through the diameter up to about 90% of the way through the diameter of the cannula. If desired, some slots can also be made fully through the wall, as long as the structural integrity of the cannula is retained. As yet another alternative, the slots can all be made on one side or at one portion of the cannula, thereby only allowing flexing in one plane or at the one cannula portion. Those of ordinary skill in the art can readily determine other suitable flexibility transition methods without undue experimentation, all of which are considered within the general teachings of the present invention.

Figure 7:
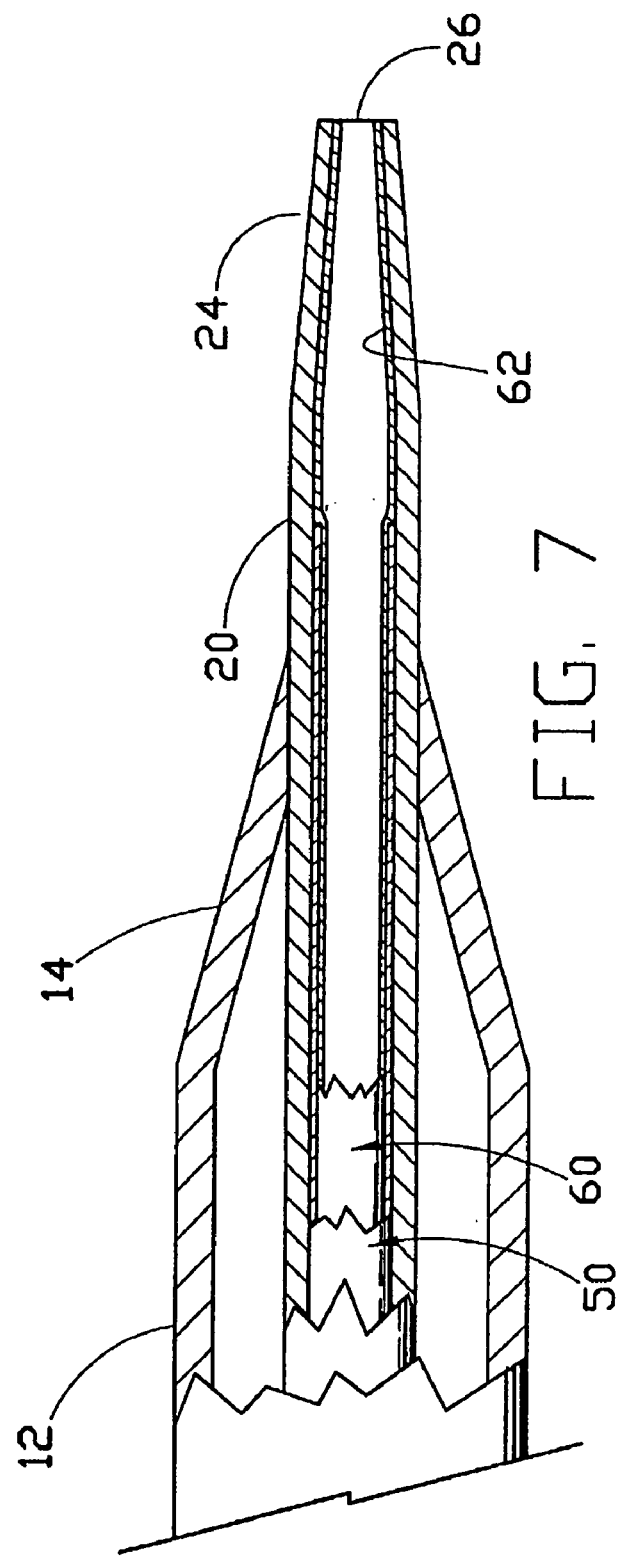
FIG. 7 is a longitudinal cross-sectional view of another embodiment of the present invention showing the addition of an inner sleeve inside of the stiffening cannula.

Another embodiment of the present invention is shown in FIG. 7. In this embodiment, an inner sleeve 60 is added interiorly of stiffening cannula 50. The distal end of inner sleeve 60 extends past the distal end of stiffening cannula 50. The distal end 62 of the inner sleeve may extend all the way to the distal end of inner cannula 20, or alternatively, may be between the respective distal ends of the inner cannula and the stiffening cannula. In either event, the distal end of the inner sleeve may be considered to extend substantially to the distal end of the inner cannula. The presence of the inner sleeve eliminates sharp edges that may be produced by the stiffening cannula. The inner sleeve also adds strength to the distal tip of the apparatus, thereby reducing the possibility of kinking and/or breakage at the tip, and reducing the abrupt change in stiffness of the prior art design.

In the embodiment of FIG. 7, it is not necessary to incorporate a spiral slot or other flexibility-enhancing feature to stiffening cannula 50. Inner sleeve 60 can be formed to have a lower coefficient of friction than the stiffening cannula, thereby facilitating passage of the wire guide through the inner lumen. If desired, inner sleeve 60 and stiffening cannula 50 can be bonded together to form a unitary piece.

In yet another alternative embodiment, inner sleeve 60 can be provided in conjunction with a spiral cut or otherwise transitioned stiffening cannula 50. If desired, inner sleeve 60 and inner cannula 20 can be formed to embed the spiral cut stiffening cannula. Inner sleeve 60 can also be used to tailor the flexibility of a spiral cut cannula, and to eliminate any sharp edges produced by a spiral cut cannula. As described herein, inner sleeve 60 can be formed from conventional biocompatible materials suitable for such a purpose, such as PTFE, nylon, or any other similar materials.

Those skilled in the art will appreciate that the sizes provided herein are examples only, and components of other sizes are also within the scope of the invention. When the apparatus of the present invention is used for catheterization, a small diameter needle, such as an 18 gauge needle, having a correspondingly short bevel tip, can be used for initial entry into the vessel. A small diameter wire guide, such as a 0.018 inch (0.46 mm) O.D. wire guide, can then be inserted through the bore of the needle, and the needle can be withdrawn. The inventive apparatus can then be slid over the small diameter wire guide and into the vessel. The smooth transition provided by the inventive apparatus between the wire guide and the larger diameter catheter (e.g., 0.039 inch O.D. or greater) minimizes trauma to the patient that might otherwise occur in the absence of such a transition. The wire guide, inner cannula and stiffening cannula can then be removed, leaving the large diameter cannula in the vessel opening. If desired, a large diameter (e.g., 0.035 or 0.038 inch O.D.) wire guide may be inserted through the lumen of the catheter, and an appropriately-sized medical device, such as a diagnostic or interventional device, can be passed into the vessel over this larger diameter wire guide. The increase in flexibility at the distal tip of the inventive apparatus enables this procedure to be performed in a manner that minimizes the trauma to the patient, and that minimizes the possibility that the distal tip portion of the apparatus will separate from the inner cannula.

While this invention has been particularly shown and described with reference to preferred embodiments thereof, it will be understood by those skilled in the art that various changes in form, details, and composition of the various components may be made therein without departing from the spirit and scope of the invention, and any such variations are considered to be within the scope of the invention. Those skilled in the art may recognize or be able to ascertain using no more than routine experimentation, many equivalents to the specific embodiments of the invention described specifically herein, which equivalents are intended to be encompassed in the scope of the invention.

The invention claimed is:

1. An apparatus for percutaneous catheterization over a wire guide, comprising:
   a catheter having proximal and distal open ends, and having a lumen extending longitudinally therethrough;
   an inner cannula having proximal and distal open ends, and having a lumen extending longitudinally therethrough, said inner cannula sized to be received within the lumen of said catheter, the distal open end of said inner cannula being sized to receive said wire guide therethrough, said inner cannula having a generally linear main body portion and a tapered distal portion, said tapered distal portion having an outer diameter that decreases toward the cannula distal end and is sized to extend through the distal open end of said catheter to provide a generally smooth diametrical transition between said catheter and said wire guide; and
   a stiffening cannula having proximal and distal open ends, and having a lumen extending longitudinally therethrough, the lumen of said stiffening cannula sized to receive said wire guide therethrough, said stiffening cannula being sized to be received within the lumen of said inner cannula and extending along the generally linear body portion of the inner cannula to a terminal point, the stiffening cannula being structured such that a distal section of said stiffening cannula has a greater flexibility than the flexibility of a proximal section of said stiffening cannula.

2. The apparatus of claim 1, wherein said stiffening cannula comprises an elongated tubular member, said tubular member comprising spiral-shaped grooves in said distal section.

3. The apparatus of claim 1, wherein said stiffening cannula comprises a wire coil disposed along an inner surface of said distal section of said stiffening cannula.

4. The apparatus of claim 1, wherein said terminal point of said stiffening cannula is between about 0.5 mm and 10 mm proximal of the distal end of the inner cannula.

5. The apparatus of claim 4, wherein said terminal point is between about 1 and 2 mm proximal of the distal end of the inner cannula.

6. The apparatus of claim 1, wherein said stiffening cannula comprises an elongated tubular member, and said stiffening cannula distal section comprises a plurality of slots formed in a surface of said tubular member.

7. The apparatus of claim 6, wherein said slots are formed along an inner surface of said tubular member.

8. The apparatus of claim 7, wherein said slots extend between about 50 and 90 percent through a diameter of said tubular member.

9. The apparatus of claim 6, wherein said slots are generally parallel and disposed along a length of the tubular member.

10. The apparatus of claim 1, wherein said stiffening cannula comprises a polymer, a metal or a composite material.

11. The apparatus of claim 1, wherein said stiffening cannula comprises first and second cannula sections, said second section being disposed distal to said first section and having greater flexibility than said first section.

12. The apparatus of claim 1, wherein said terminal point is proximal to the distal end of said inner cannula, and wherein said apparatus further comprises an inner sleeve, said inner sleeve having proximal and distal open ends and a lumen extending longitudinally therethrough, said inner sleeve being sized to be received within the lumen of said stiffening cannula, and extending beyond said stiffening cannula in the distal direction.

13. An apparatus for percutaneous catheterization, comprising:
   a catheter having proximal and distal open ends, and having a lumen extending longitudinally therethrough;
   an inner cannula having proximal and distal open ends, and having a lumen extending longitudinally therethrough, said inner cannula sized to be received within the lumen of said catheter, the distal open end of said inner cannula being sized to receive a wire guide therethrough, said inner cannula having a generally linear main body portion and a tapered distal portion, said tapered distal portion having an outer diameter that decreases toward the cannula distal end and is sized to extend through the distal open end of said catheter to provide a generally smooth diametrical transition between said catheter and said wire guide;
   a stiffening cannula having proximal and distal open ends, and having a lumen extending longitudinally therethrough, said stiffening cannula being sized to be received within the lumen of said inner catheter; and
   an inner sleeve having proximal and distal open ends, and having a lumen extending longitudinally therethrough, the lumen of said inner sleeve sized to receive said wire guide therethrough, said inner sleeve being sized to be received within the lumen of said stiffening cannula, said inner sleeve distal end extending substantially to said distal opening of said inner cannula.

14. The apparatus of claim 13, wherein said stiffening cannula has a distal section of greater flexibility than the flexibility of a proximal section of said stiffening cannula.

15. The apparatus of claim 13, wherein said stiffening cannula extends along the generally linear body portion of the inner catheter to a terminal point between about 0.5 mm and 10 mm proximal of the distal open end of the inner cannula, and wherein said inner sleeve extends substantially to said inner cannula open end.

16. The apparatus of claim 15, wherein said terminal point is between about 1 and 2 mm proximal of said distal open end.

17. The apparatus of claim 14, wherein said stiffening member comprises an elongated tubular member having a spiral shaped groove formed at said distal section.

18. A method of percutaneous catheterization, comprising the steps of:
   introducing a wire guide into a vessel;
   providing a catheterization apparatus, said apparatus comprising: a catheter having a lumen extending longitudinally therethrough and having a distal end; an inner cannula having a lumen extending longitudinally therethrough, said inner cannula sized to be received within the lumen of said catheter, a distal end of said inner cannula tapering to a diameter just large enough to enable said wire guide to pass freely therethrough, said tapered distal end providing a generally smooth diametrical transition between said catheter and said wire guide; and a stiffening cannula having a lumen extending longitudinally therethrough, the lumen of said stiffening cannula sized to receive said wire guide therethrough, said stiffening cannula being sized to be received within the lumen of said inner catheter, the stiffening cannula being structured such that a distal section of said stiffening cannula has a greater flexibility than the flexibility of a proximal section;

introducing said apparatus into said vessel over said wire guide; and withdrawing said wire guide, inner cannula and stiffening cannula from said vessel, while maintaining said catheter in said vessel.

19. The method of claim 18, wherein said wire guide comprises a first wire guide, said method further comprising the steps of inserting a second wire guide into said vessel through said lumen of said catheter following withdrawal of said first wire guide, inner cannula and stiffening cannula, said second wire guide having a larger outer diameter than that of said first wire guide; and inserting a medical device into said vessel over said second wire guide.

20. The method of claim 18, wherein said wire guide is introduced into the vessel over a needle via the Seldinger technique.

* * * * *